US011925447B1

(12) United States Patent
Patel et al.

(10) Patent No.: US 11,925,447 B1
(45) Date of Patent: Mar. 12, 2024

(54) OUT-OF-BED ZONE GENERATION AND MONITORING ASSOCIATED WITH RESPIRATORY ACTIVITY TRACKING

(71) Applicant: Amazon Technologies, Inc., Seattle, WA (US)

(72) Inventors: Pratik Kalpesh Patel, San Jose, CA (US); Feng Zhang, Greenbelt, MD (US); Koohyun Um, Sunnyvale, CA (US); James J. Wolfe, San Jose, CA (US)

(73) Assignee: Amazon Technologies, Inc., Seattle, WA (US)

( * ) Notice: Subject to any disclaimer, the term of this patent is extended or adjusted under 35 U.S.C. 154(b) by 354 days.

(21) Appl. No.: 17/183,773

(22) Filed: Feb. 24, 2021

(51) Int. Cl.
*A61B 5/05* (2021.01)
*A61B 5/00* (2006.01)
*A61B 5/11* (2006.01)
*A61B 5/113* (2006.01)
*G01S 13/62* (2006.01)
*G16H 40/67* (2018.01)
*G16H 50/30* (2018.01)

(52) U.S. Cl.
CPC .............. *A61B 5/05* (2013.01); *A61B 5/1115* (2013.01); *A61B 5/113* (2013.01); *A61B 5/4806* (2013.01); *G01S 13/62* (2013.01); *G16H 40/67* (2018.01); *G16H 50/30* (2018.01); *A61B 5/1128* (2013.01)

(58) Field of Classification Search
CPC . G01S 7/41; G01S 13/56; G01S 13/87; G01S 13/88; G01S 7/415; A61B 5/05; A61B 5/0507; A61B 5/1102; A61B 5/113; A61B 5/4812; A61B 5/4818; A61B 7/003; A61B 5/0026; A61B 5/0205; A61B 5/11; A61B 5/1118; A61B 5/4806; A61M 2205/609
See application file for complete search history.

(56) References Cited

U.S. PATENT DOCUMENTS

| 2013/0135137 A1* | 5/2013 | Mulder | G01S 3/48 342/28 |
| 2018/0106897 A1* | 4/2018 | Shouldice | A61B 5/4818 |
| 2023/0043406 A1* | 2/2023 | Zhang | A61B 5/1102 |

* cited by examiner

*Primary Examiner* — Matthew Kremer
*Assistant Examiner* — Elina Sohyun Ahn
(74) *Attorney, Agent, or Firm* — Lowenstein Sandler LLP

(57) ABSTRACT

A method and system including a monitoring device to detect, during a session, a set of radar signals associated with first respiratory-related movements of a first person and second respiratory-related movements of a second person located within a detection zone comprising at least a portion of a bed. The method and system dynamically generate an out-of-bed zone adjacent to a side of the bed. The out-of-bed zone is monitored to detect motion within the zone to determine when the first person exits and enters the bed. The method and system identify a portion of the set of radar signals collected during a time period when the first person is determined to be out of the bed. The identified portion of the set of radar signals is removed from the set of radar signals collected during the sleep session.

16 Claims, 7 Drawing Sheets

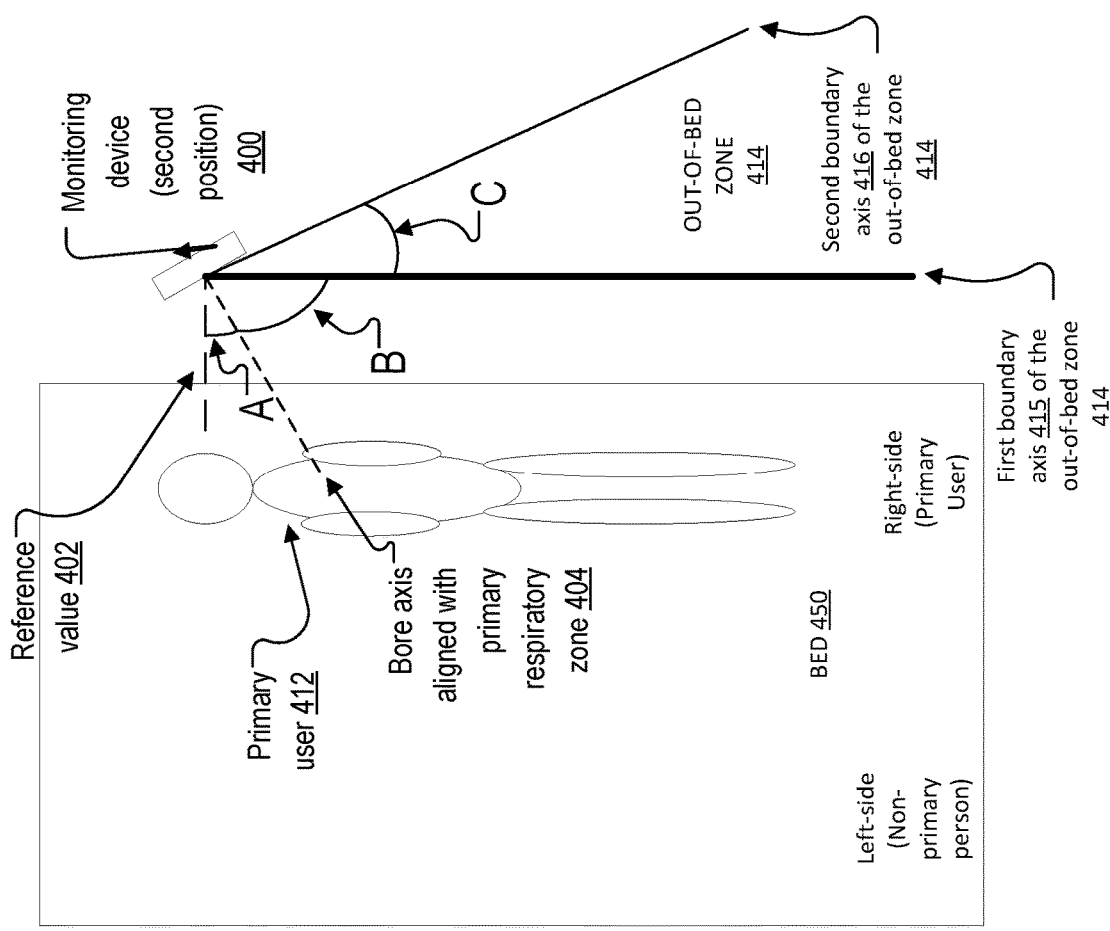
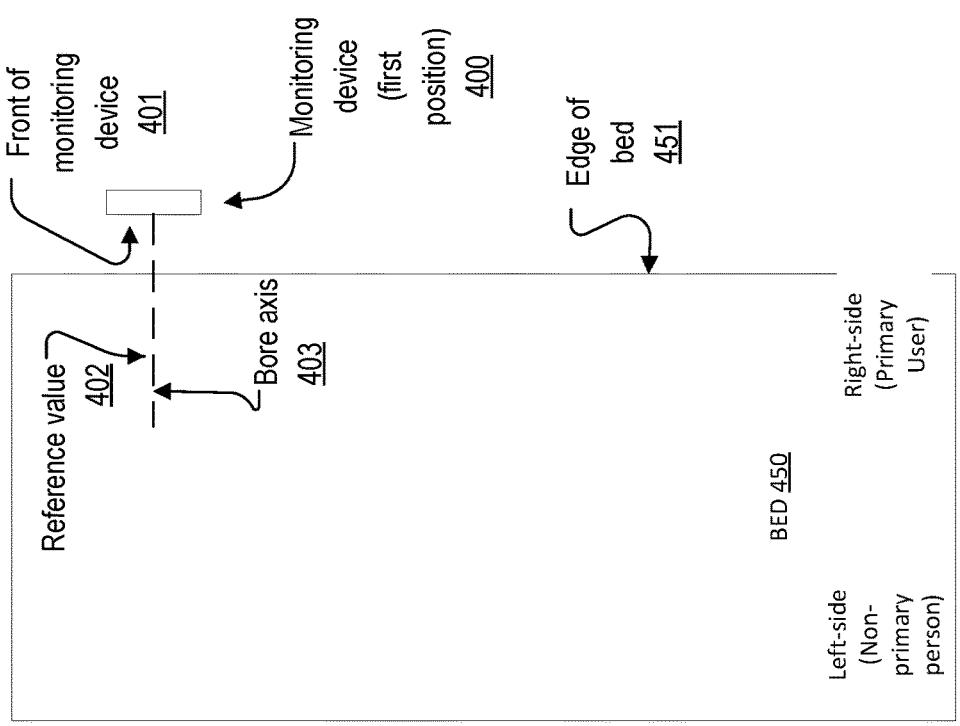
Figure 4B
Figure 4A

OUT-OF-BED ZONE GENERATION AND MONITORING ASSOCIATED WITH RESPIRATORY ACTIVITY TRACKING

BACKGROUND

Respiratory monitoring devices are used to track a user's breathing activity and patterns while the user sleeps. The respiratory activity tracking can be used to identify sleep patterns (e.g., generate sleep scores and hypnograms) and monitor issues relating to cardiovascular or respiratory diseases or conditions. The sensing device is typically positioned next to the user's bed (e.g., on a nightstand adjacent to the bed) and uses radar to detect movement within a detection zone to identify a respiratory waveform of the user primary user.

Typical detection zones provide monitoring coverage that includes at least a portion of the bed where an intended or the primary user (e.g., a user for which sleep activity tracking is intended) sleeps and at least a portion of an area where a second person typically sleeps. These sensing devices are configured to track the respiration of the user closest to the device and does not discriminate between users. As such, when two people are in the detection zone of the device and the primary user leaves the bed during the monitoring period, the device automatically starts tracking the other person in the detection zone. This produces false-positive readings and sleep-session data that is a combination of both the primary user and the non-primary user. In addition, the detection zone established based on the orientation of the sensing device can be under-sized or inaccurately aligned (e.g., pointing at a region of the detection zone typically including a leg of the primary user) and fail to include a necessary level of coverage to the side of the bed to identify exit from or entry into the bed by the primary user.

BRIEF DESCRIPTION OF DRAWINGS

The present disclosure will be understood more fully from the detailed description given below and from the accompanying drawings of various embodiments, which, however, should not be taken to limit the present disclosure to the specific embodiments, but are for explanation and understanding only.

FIGS. 4A and 4B illustrate a monitoring device and detection zone in example stages of a method for generating and monitoring an out-of-bed zone associated with a sleeping environment to identify out-of-bed zone entry and exit events, according to one or more embodiments, according to one or more embodiments.

DETAILED DESCRIPTION

Figure 1:
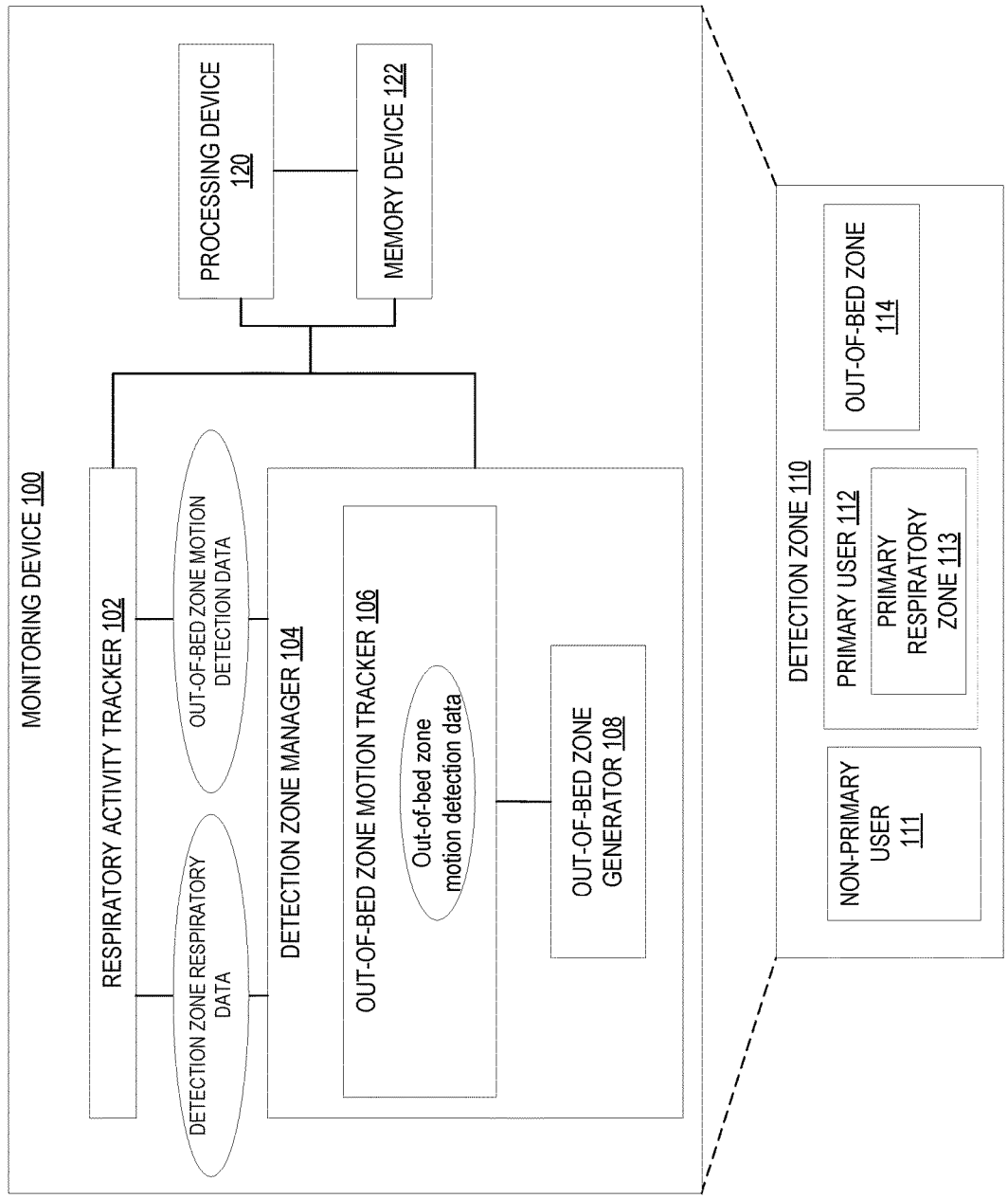
FIG. 1 illustrates an example environment including a monitoring device to monitor respiratory activity of a user in a detection zone including a generated out-of-bed zone to detect out-of-bed activity, according to one or more embodiments.

The present disclosure relates to a method and system to monitor respiratory activity of an intended or primary user during a sleep session by establishing a detection zone including a dynamically generated out-of-bed zone (e.g., a zone or area located on the side of a bed associated with the primary user). The method and system include a monitoring device to detect motion associated with the out-of-bed zone to determine when the primary user exits the bed (e.g., changes from a sleeping position to a non-sleeping position) and when the primary user enters the bed (e.g., establishes a sleeping position).

The method and system generate out-of-bed zone motion indicator data including timestamp information associated with motion of the primary user within the out-bed-zone (e.g., identification of a time associated with a peak amplitude of a radar signals associated with motion of the primary user within the out-of-bed zone). In an embodiment, the out-of-bed zone motion data can include a first timestamp identifying a first time associated with radar signals corresponding to motion of the primary user within the out-of-bed zone. In an embodiment, the out-of-bed zone entry data includes a second timestamp identifying a second time when the primary user exited the out-of-bed zone and re-entered the bed.

In an embodiment, a set of sleep monitoring data for a sleep session can be updated or adjusted in view of the out-of-bed zone entry data and out-of-bed zone exit data. In an embodiment, a portion of the sleep monitoring data corresponding to a time period between the first timestamp (e.g., the first time associated with a first out-of-bed zone motion detection indicator) and the second timestamp (e.g., the second time associated with a second out-of-bed zone motion detection indicator) is removed from the set of sleep monitoring data for the particular sleep session.

In an embodiment, the monitoring device generates an out-of-bed zone adjacent to a side of the bed associated with the primary user. The out-of-bed zone includes a region between a first boundary axis and a second boundary axis. In an embodiment, the monitoring device generates the out-of-bed zone by identifying the first boundary axis of the out-of-bed zone and the second boundary axis of the out-of-bed zone relative to a primary respiratory zone associated with a primary user. In an embodiment, the primary respiratory zone includes a portion of the bed corresponding to collected respiratory-related radar signals associated with respiratory movements of the primary user. As described in greater detail below, the primary respiratory zone can be identified in accordance with a first approach (described with reference to FIGS. 3, 4A, and 4B) or a second approach (described with reference to FIG. 5).

In an embodiment according to a first approach, during a setup phase, the monitoring device is arranged in a first position wherein a front of the monitoring device is parallel to a side or edge of a bed associated with the primary user (e.g., a side of the bed that the primary user typically sleeps). In the first position, a bore axis of the monitoring device is in an at least substantially perpendicular alignment relative to an edge of the side of the bed. In the first position, with the bore axis in perpendicular alignment with the edge of the side of the bed, the monitoring device determines a first value of the bore axis (also referred to as a "reference value"). In an embodiment, the first value of the bore axis is an azimuth angle representing an angular measurement in a spherical coordinate system. In an embodiment, since the first value of the bore axis is used as a reference or baseline value, the first value of the bore axis of the monitoring device in the first position is represented as a 0° azimuth angle (e.g., a reference azimuth angle value of the bore axis when the monitoring device is in the first position).

In an embodiment, the monitoring device is then rotated from the first position to a second position such that the bore axis of the monitoring device is at least substantially aligned and directed with a portion of the bed corresponding to a location of a chest of the primary user when the primary user is in a usual or typical sleeping position (herein referred to as a "primary respiratory zone"). Advantageously, aligning the bore axis of the monitoring device with the primary respiratory zone enables collection of high quality radar signals associated with respiratory movement of the primary user during a sleep session.

In an embodiment, in the second position, the monitoring device identifies a second value of the bore axis corresponding to the alignment of the bore axis with the primary respiratory zone. In an embodiment, the second value of the bore axis in the second position is an azimuth angle value (in degrees) that is measured relative to the first value (i.e., the reference value of 0°) of the bore axis when the monitoring device is in the first position. For example, the second value of the bore axis can be represented as an angular measurement in the spherical coordinate system relative to the baseline or reference angle associated with the first value of the bore axis.

In an embodiment, the monitoring device uses the first value of the bore axis and the second value of the bore axis to determine a first angle value corresponding to an arc length between the bore axis in the first position (e.g., a first side) and the bore axis in the second position. In an embodiment, one or more sensors of the monitoring device (e.g., inertial measurement unit sensors, magnetometer sensors, etc.) can determine the rotation of the monitoring device from the first position to the second position. The measured rotation of the monitoring device corresponding to rotation from the first position to the second position can be used to determine the first angle value, where the first angle value corresponds to a first angle formed by the bore axis in the first position and the bore axis in the second position diverging from a common vertex point (e.g., the monitoring device in the second position).

In an embodiment, the monitoring device determines a second angle value based on the first angle value. The second angle value is an arc length determined by calculating a difference between a right angle value (i.e., a 90° angle value) and the first angle value. In an embodiment, a position of a first boundary axis of the out-of-bed zone is determined by spanning the second angle value from the bore axis when the monitoring device is in the second position (e.g., in alignment with the primary respiratory zone). In an embodiment, a second angle having the second angle value is formed between the bore axis of the monitoring device in the second position and the first boundary axis.

In an embodiment, a position of a second boundary axis of the out-of-bed zone is determined by spanning an offset arc length (e.g., 20° to 90°) from the position of the first boundary axis. In an embodiment, a third angle is formed between the first boundary axis and the second boundary axis diverging from the monitoring device in the second position (e.g., the vertex point of the third angle). In an embodiment, the third angle corresponds to the out-of-bed zone that is monitored by the monitoring device to detect motion.

In an embodiment according to a second approach, the monitoring device can identify the primary respiratory zone based on historical respiratory movement-related radar signals collected during one or more sleep sessions. In this embodiment, during a setup phase, the monitoring device can identify (e.g., based on an input or indication to a prompt during a setup routine from a user) which side of the bed (e.g., by providing an input to a prompt during a setup routine) the monitoring device is located. During use of the monitoring device to monitor respiratory activity within a detection zone, a primary respiratory zone associated with a primary user is identified. In an embodiment, the primary respiratory zone is identified as a location within the detection zone having a highest concentration of radar signals having a highest relative signal strength.

In an example, the primary respiratory zone can be identified based on a voxel mapping associated with the respiratory-related movement data of the primary user. In this embodiment, the voxel mapping of respiratory-related radar signals is analyzed to determine an axis line corresponding to an approximate centroid of the voxel mapping. In an embodiment, a long term average of multiple axis lines aligned with centroid values of collected radar data (e.g., imaging radar configured to locate respiration motion in a 3D space corresponding to the detection zone) is determined and used to identify the primary respiratory zone.

According to embodiments, the method and system can establish a primary respiratory zone aligned with a source of the radar signals corresponding to respiratory movements of the primary user. Advantageously, the method and system can determine an optimized out-of-bed zone (e.g., an area adjacent to the bed) relative to the primary respiratory zone that is monitored to identify movement of the primary user into and out of the generated out-of-bed zone (e.g., exiting and re-entering the bed). The out-of-bed zone entry data and out-of-bed zone exit data are used during the processing of the sleep-session data. Advantageously, the accuracy of the sleep-session data is improved by targeting the activity of the primary user. In this regard, the primary user's activity is targeted by establishing an out-of-bed zone aligned with a side of the bed and monitoring out-of-bed zone entry and exit indicators to account for instances where the primary user enters and exits the out-of-bed zone (e.g., is out of the bed and the respiratory activity tracking zone).

In an embodiment, respiratory activity data associated with a time period during which the primary user is out of the bed (e.g., a time period between entry into the out-of-bed zone and exit from the out-of-bed zone) can be removed from the set of respiratory activity data that is processed for purposes of analyzing the primary user's sleep data (e.g., determining a sleep score, identifying sleeping patterns, etc.).

As described above, the embodiments described herein overcome problems and challenges with respect to conventional sleep monitoring processing by dynamically determining an optimized out-of-bed zone corresponding to the side of a bed to track movement of an primary user exiting and entering the bed. The out-of-bed activity is accounted for in processing the respiratory activity data of the primary user during a sleep session. In an embodiment, the respiratory data corresponding to a time period when the primary user is not in the bed (e.g., a time period between when the primary user has entered the out-of-bed zone and exited the out-of-bed zone and re-entered the bed) is removed from the overall set of respiratory data. Removal of the respiratory activity data corresponding to the out-of-bed activity enables the reduction of false-positives associated with a non-primary user.

FIG. 1 illustrates an example environment including a monitoring device 100 configured to monitor sleep activity data associated with an intended or primary user in a detection zone 110 including a sleeping environment (e.g., a bed). In an embodiment, the monitoring device 100 can include a respiratory activity tracker 102, a detection zone manager 104, an out-of-bed zone motion tracker 106, and an out-of-bed zone generator 108. In an embodiment, the monitoring device 100 is a computing device including one or more processing devices 120 and one or more memory devices 122 configured to store and execute instructions to perform the functions and operations performed by the detection zone manager 104, the out-of-bed zone motion tracker 106, and the out-of-bed zone generator 108, described in detail herein. According to an embodiment, the monitoring device 100 includes one or more sensors (e.g., inertial measurement unit (IMU) sensors, magnetometer sensors, radar sensors, motion detectors, etc.) to collect and process data corresponding to a detection zone 110 to monitor the respiratory activity of a primary user within the detection zone 110.

According to embodiments, the respiratory activity tracker 102 includes one or more radar-based sensors to receive signals corresponding to respiratory-related motion occurring within a detection zone 110. In an embodiment, the respiratory activity tracker 102 includes one or more millimeter wave (MM wave) radar sensors to detect a respiration waveform of a person located within the detection zone 110. In an embodiment, the respiration waveform can be detected according to a suitable waveform extraction algorithm (e.g., a Doppler radar for noncontact vitals monitoring methodology). For example, the waveform extraction algorithm can include a multistage processing of radar outputs raw In-phase and Quadrature (I/Q) data of received echo signals. In an embodiment, the one or more radar sensors are used to "bin" the receive signals such that the receive signal returns are sored into a set of bins by time of arrival relative to a transmit pulse. In an embodiment, the respiratory activity tracker 102 checks the receive signal strength in the respective bins to enable the sorting of the returns across the different bins, which correspond to different ranges.

In an embodiment, a range fast Fourier Transform (FFT) is implemented over these samples (a fast-time domain) to identify a channel response for each distance bin. In this example, another FFT is implemented over the frames within the respiration window (slow-time domain) for a set of candidate bins to determine which bin contains the respiration signal. In an embodiment, the bin corresponding to the desired respiration signal is selected based on a metric for a periodicity and a phase of that bin along the time domain to identify a selected or target waveform to be extracted.

In an embodiment, the one or more sensors of the respiratory activity tracker 102 extract the periodic signals within a field of view (e.g., the detection zone 110) of the monitoring device 100 and uses out-of-bed information to distinguish signals corresponding to a primary user and a non-primary user within the detection zone, as described in greater detail below.

In an embodiment, the respiratory activity tracker 102 selects a location within the detection zone 110 of the monitoring device 100 corresponding to a combination of a higher relative signal strength and a likeness or similarity to baseline or reference vitals signals. In an embodiment, the respiratory activity tracker 102 selects signals corresponding to a respiratory waveform of a primary candidate source (e.g., the primary user) based on combination of metrics implemented at low level processing of the radar return signals.

In an embodiment, the one or more sensors of the respiratory activity tracker 102 measure a displacement of a user's chest to identify a respiratory rate associated with the user. In an embodiment, the respiratory activity tracker 102 uses three-dimensional imaging to generates a set of energy voxels corresponding to chest displacement movements and periodicity corresponding to a breathing pattern of the user. In an embodiment, the set of energy voxels are processed by the respiratory activity tracker to generate the respiration or breathing waveform corresponding to the user during a given sleep session.

In an embodiment, the respiratory activity tracker 102 can generate a respiration waveform representing a respiratory rate or number of breaths a user takes per minute. In an embodiment, the respiratory rate data and associated waveform can be further processed to generate one or more analytics indicative of a quality of sleep of the primary user. For example, the respiration waveform can be analyzed to generate a sleep score (e.g., an indication or score indicative of a quality of sleep). In an embodiment, a sleep score can be determined in accordance with a suitable sleep score generation methodology as a function of one or more factors including an overall sleep time, a duration of the REM sleep stage, a duration of a light sleep stage, a duration of a deep sleep stage, etc. In an embodiment, the sleep stages can be estimated using a deep neural network which takes the respiration waveform as the input.

In an embodiment, the detection zone manager 104 uses the one or more radar sensors of the monitoring device 100 to determine and monitor the detection zone 110. In an embodiment, the detection zone 110 is an area or region corresponding to a field of view of the one or more radar sensors of the monitoring device 100 (e.g., an area or region corresponding to a field of view angle of the monitoring device 100). In an embodiment, one or more radar sensors of the monitoring device 100 performs a localization of reflected signal in the 3D geometry, which is further subdivided into voxels. A voxel is a discrete volume element of graphic information in a three-dimensional (3D) space. The voxel can be used in the radar domain to represent the smallest volume element governed by a combination of range and angular resolution (e.g., also referred to as a range bin, angular bin individually in a 2D space). Each voxel carries information derived from a phase and amplitude of reflected signal from corresponding geometric volume in the real world. In an embodiment, the front of the radar sensors of the monitoring device 100 are parallel to the edge of the bed and the detection zone corresponds to the bed area within the field of view of the radar sensors. In an embodiment, the detection zone 110 can be estimated from a distribution of the coordinates of a selected voxel for respiration waveform extraction. In this embodiment, the diversity of the primary user's 112 overnight motion is utilized. In an embodiment, the selected voxels can belong to the bed area which corresponds to the detection zone 110. In an embodiment, a default detection zone 110 can be programmed for a given system based on signal quality criteria for a given application.

In an embodiment, the detection zone 110 includes at least a portion of a bed or other sleeping environment associated with a primary user 112 and a non-primary user 111. In an embodiment, the detection zone manager 104 identifies the detection zone 110 or area within the field of view of the one or more radar sensors that is monitored for purposes of collecting respiratory signals during a sleep session. In an embodiment, during a sleep session (e.g., a period of time during which respiratory activity within the detection zone 110 is monitored), respiratory activity of both the primary user 112 and the non-primary user 111 can be detected. For example, the detection zone manager 104 can include one or more radar sensors configured to track the respiration of a user closest to the monitoring device 100 (i.e., the primary user 112). In an embodiment, when the primary user 112 leaves the bed (e.g., to get a drink of water or use the restroom), the monitoring device 100 tracks the respiratory activity of a next closest user (e.g., the non-primary user 111) in the detection zone 110.

In an embodiment, the detection zone manager 104 identifies and monitors a primary respiratory zone 113 associated with the primary user 112. In an embodiment, as described below with reference to FIGS. 4A and 4B, the primary respiratory zone 113 can be identified based on an orientation or position of the monitoring device 100 as set during a setup phase of a process to generate the out-of-bed zone. In an embodiment, during the setup phase, the monitoring device 100 can be placed next to a side of the bed on which the primary user 112 typically sleeps when the bed is occupied by multiple persons. In an embodiment, when the primary user 112 is positioned in the bed, the placement of the monitoring device 100 at the side of the bed associated with a primary user enables a "shadowing" or blocking of radar detection signals associated with the non-primary user 111. For example, for a 60 GHz radar sensor, a large portion of the radar signals get reflected back from the primary user 112, while the body of primary user 112 blocks transmission of the radar signals to the non-primary user.

Figure 2:
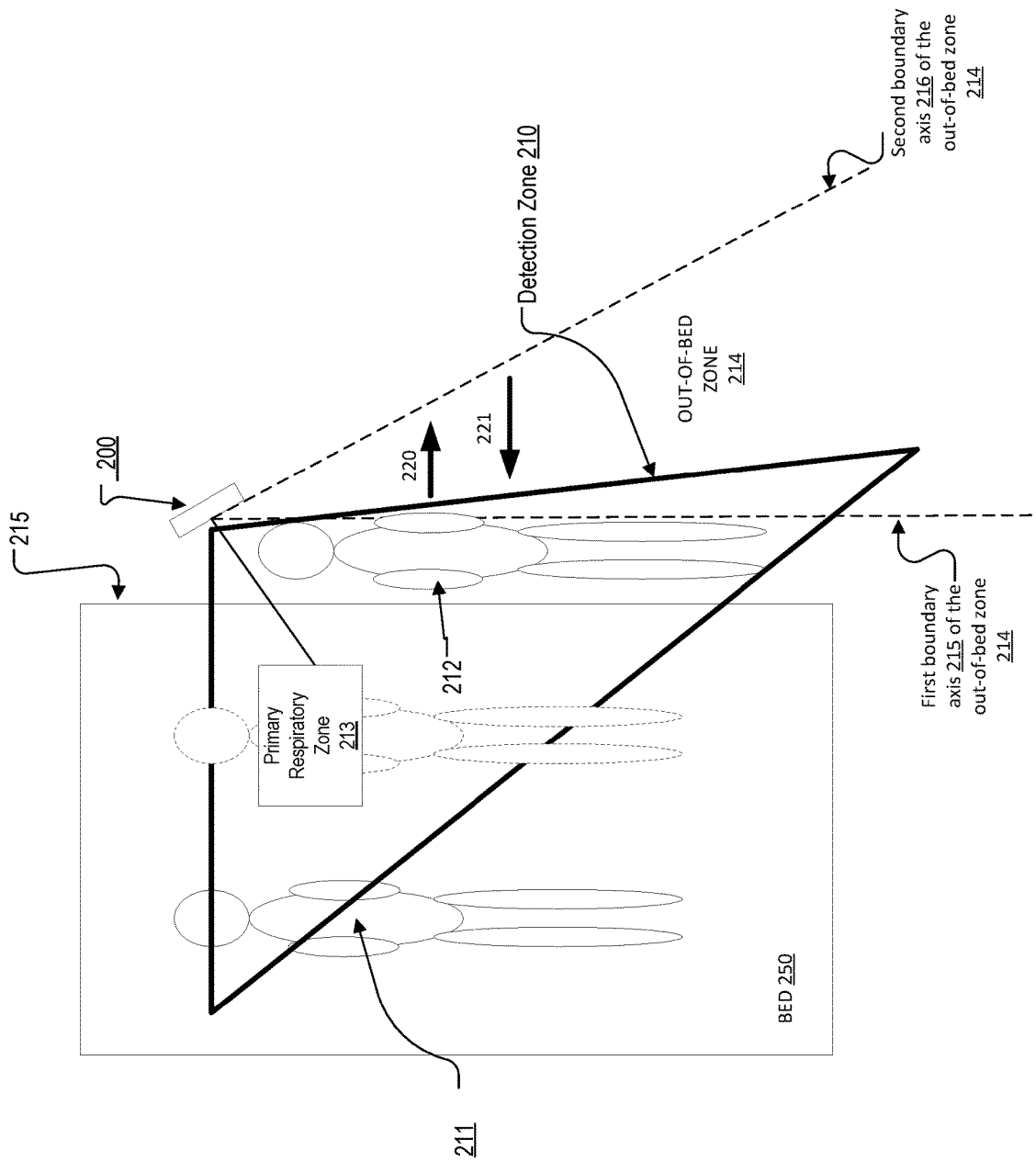
FIG. 2 illustrates an example of generating and monitoring an out-of-bed zone associated with a sleeping environment to identify out-of-bed zone motion detection data, according to one or more embodiments.

The out-of-bed zone generator 108 includes one or more sensors configured to generate an out-of-bed zone 114 adjacent to a side of the bed, according to embodiments of the present disclosure described in greater detail below. In an embodiment, the out-of-bed zone 114 includes an area next to the side edge of the bed (as shown in FIG. 2) which corresponds to a side of the bed on which the primary user 112 typically sleeps when the bed is occupied by both a primary user 112 and non-primary user. In an embodiment, the out-of-bed zone 114 is a region or area between a first boundary axis and a secondary axis associated with the monitoring device, as shown, for example, in FIGS. 2 and 4.

In an embodiment, the out-of-bed zone generator 108 is configured to execute one or more processes to identify an angle corresponding to the out-of-bed zone formed by the first boundary axis and the second boundary axis, as described in greater detail below with reference to FIGS. 2-5.

In an embodiment, the out-of-bed zone motion tracker 106 includes one or more inertial measurement unit (IMU) sensors or one or more magnetometer sensors to measure an angular rotation of the monitoring device 100 upon rotation from a first position or orientation (i.e., a position where a bore axis of the monitoring device 100 is arranged in a substantially perpendicular manner relative to a side edge of the bed) to a second position or orientation (i.e., a new position of the monitoring device 100 following rotation from the first position where a bore axis of the monitoring device 100 is aligned with a location within the bed where a chest of the primary user 112 is located when the primary user 112 is in a typical lying or sleeping position in the bed).

In an embodiment, the out-of-bed zone motion tracker 106 includes one or more radar sensors to monitor and identify motion of the primary user as he or she enters and exits the out-of-bed zone 114. In an embodiment, the out-of-bed zone motion tracker 106 performs a radar-based detection of motion of an object (e.g., the primary user 112) within the out-of-bed zone 114. In an embodiment, a set of radar signals associated with motion of a target object within the out-of-bed zone.

In an embodiment, the one or more radar sensors generate a 3D point cloud when motion of a target object is detected. Each point in the point cloud corresponds to the radar signal reflected by a part of the body of the target object. In an embodiment, the 3D point cloud tracks a trajectory of the movement of the target object in real-time. When a largest portion of the point cloud (e.g., a majority portion) is detected within the out-of-bed zone 114, the motion into the out-of-bed zone is detected. In an embodiment, the monitoring device 100 detects a transition of the location (centroid) of the 3D point cloud between the out-of-bed zone 114 and detection zone 110 to determine if the primary user 112 is entering or exiting the bed. In an embodiment, the monitoring device 100 can determine a volume of the point cloud of the target being tracked. In an embodiment, the relative volume of the point cloud can be used distinguish between a human and a common pet or inanimate object (e.g., a slipper, a pillow, etc.) since the human has a relatively higher point cloud volume than the average pet or other object.

In an embodiment, the motion within the out-of-bed zone 114 can be detected by identifying a peak amplitude of a distribution of reflected radar signals (e.g., as a function Doppler frequency or Doppler velocity) in a radar power spectrum (e.g., a Doppler spectrum). For example, the monitoring device 100 can identify a first time corresponding to a first peak amplitude of a distribution of reflected radar signals corresponding to motion of an object (e.g., the primary user 112) with the monitored out-of-bed zone 114. In an example, the monitoring device 100 can identify a second time corresponding to a first peak amplitude of a distribution of reflected radar signals corresponding to motion of an object (e.g., the primary user 112) with the monitored out-of-bed zone 114. The first time and the second time can be collected as part of the out-of-bed zone motion detection data.

In an embodiment, motion within the out-of-bed zone 114 can be detected by identifying an overlap of a 3D point cloud corresponding to motion of a target object and the out-of-bed zone 114. In an embodiment, motion within the out-of-bed zone 114 can be detected by tracking a trajectory of the 3D point cloud using a suitable tracking algorithm.

In an embodiment, the out-of-bed zone motion tracker 106 generates information corresponding to the object's motion within the out-of-bed zone 114, herein referred to as an out-of-bed zone motion detection data. In an embodiment, the out-of-bed zone motion detection data includes a timestamp generated in response to identifying peak amplitudes of a set of radar signals corresponding to motion of the object (e.g., the primary user) within the out-of-bed zone are detected. In an embodiment, the out-of-bed zone motion detection data can include timestamps associated with motion by an object in the out-of-bed zone. In an embodiment, the motion can be detected by determining the volume of the point cloud associated an object moving within the out-of-bed zone is greater than a predetermined threshold level.

In an embodiment, the out-of-bed zone motion detection data is used to identify a time period when the primary user 112 is out of the bed (also referred to as an "out-of-bed period"). In an embodiment, when the primary user 112 is absent from the bed, the detection zone manager 104 continues to detect respiratory-related activity data corresponding to the non-primary user 111 and/or related noise signals. In an embodiment, since at least a portion of the non-primary user 111 is within the detection zone 110, the one or more radar sensors of the detection zone manager 104 switch to detection of the respiratory-related movements of the non-primary user 111 when the primary user 112 has vacated the bed. In an embodiment, although the relative strength of the radar signals received in connection with the respiratory-related movements of the non-primary user 111 may be less than the radar signals associated with the primary user 112, the radar signals relating to the non-primary user 111 are collected during the time period when the primary user is out of the bed.

In an embodiment, when both a primary user 112 and a non-primary user 111 occupy the bed, the monitoring device 100 identifies a strongest relative respiration signal within the detection zone 110. In an embodiment, since the primary user 112 is closer to the monitoring device 100 and the line-of-sight path between the non-primary user 111 and the monitoring device 100 can be at least partially blocked by the primary user 112, the signal reflected by the primary user 112 is relatively stronger than that reflected by non-primary user 111. Accordingly, the respiratory-related movements of the primary user 112 are detected during periods when both the primary user 112 and the non-primary user 111 occupy the bed. In an embodiment, when the primary user 112 leaves the bed, the respiration-related radar signals of the non-primary user 111 are picked up (e.g., as being the current strongest relative respiration signal). As such, respiratory-related radar signals collected during a given sleep session can include a combination of radar signals associated with the primary user 112 and the non-primary user 111.

In an embodiment, the respiratory activity tracker 102 receives the out-of-bed zone motion detection data and removes a corresponding set of respiratory data collected during the out-of-bed period from the overall respiratory data collected during the sleep session. This enables the motion of the primary user 112 to be tracked and monitored to eliminate false-positive readings (e.g., respiratory data corresponding to another person in the detection zone) collected when the primary user 112 is not in the bed.

For example, when the primary user 112 exits the bed, first motion associated with the primary user 112 is detected within the out-of-bed zone 114 at a first time. In this example, when the primary user 112 returns to the bed, second motion associated with the primary user 112 is detected within the out-of-bed zone 114 at a second time. In an embodiment, the out-of-bed zone motion tracker 106 generates out-of-bed zone motion detection data including the first time and the second time associated with the first motion and the second motion of the primary user 112 within the out-of-bed zone 114.

In an embodiment, if the primary user 112 is alone in the bed (e.g., there is a single user), the out-of-bed information can continue to be tracked and the radar signals (e.g., noise signals) collected when the primary user 112 is absent from the bed can be identified and marked to indicate that no person was present in the bed during the corresponding time period.

In an embodiment, multiple out-of-bed periods (e.g., multiple pairs of detection motion events within the out-of-bed zone 114) can be identified in connection with a single sleep session. For each time period during which the monitoring device 100 determines the primary user 112 is not in the bed (e.g., in view of motion detected within the out-of-bed zone 114), the respiratory data collected during the one or more out-of-bed periods can be removed from the overall respiratory data that is processed by the respiratory activity tracker 102. This results in a more accurate and refined measurement and analysis of the respiratory activity data collected during a sleep session. In particular, processing of the respiratory activity data collected during the sleep session is improved by filtering out data associated with a non-primary user that is collected during one or more periods of time when the primary user 112 is out of the bed. Furthermore, noisy respiratory related radar signals detected in response to movement of the primary user as he or she transitions into and out of the bed can be identified and removed from the set of respiratory-related radar signals during subsequent processing. Accordingly, a final or overall set of respiratory activity data can be generated and stored that includes the respiratory activity data of the primary user, while removing any respiratory activity data collected while the primary user is out of the bed.

FIG. 2 illustrates an example environment including a monitoring device 200, according to embodiments of the present disclosure. In an embodiment, the monitoring device 200 includes the components described in connection with monitoring device 100 of FIG. 1. In an embodiment, the monitoring device 200 is configured to identify and establish a detection zone 210 which is monitored to identify respiratory-related movements occurring within the detection 210 during a period of time (also referred to as a "sleep session"). In an embodiment, the detection zone 210 includes at least a portion of a sleeping environment (e.g., a bed 250). In the embodiment shown in FIG. 2, the bed 250 includes multiple people: a primary user 212 and a non-primary user 211. In an embodiment, the monitoring device 200 is configured to generate a set of respiratory activity data associated with the primary user 212. However, as shown, the detection zone 210 can include coverage of a typical sleeping position of the non-primary user 211.

In an embodiment, the monitoring device 200 is arranged on a side of the bed 250 on which the primary user 212 typically sleeps (e.g., a right-side of the bed from the overhead perspective shown in FIG. 2). In an embodiment, the monitoring device 200 includes one or more radar sensors configured to detect radar signals corresponding to respiratory-related movements (e.g., movements of the chest associated with breathing) within the detection zone. In an embodiment, the monitoring device 200 detects and tracks the respiratory activity data (e.g., data corresponding to the respiratory-related movements of an object) associated with the primary user 212. In an embodiment, the monitoring device 200 detects and tracks the radar signals corresponding to a closest object to the monitoring device 200 that provide a radar signal strength that exceeds a threshold signal strength level.

In an embodiment, if the primary user 212 exits the bed 250 during a sleep session, the monitoring device 200 continues to detect respiratory-related movements within the detection zone 210. For example, when the primary user 212 is out of the bed 250, an updated closest radar signal source (or updated highest relative strength radar signal) can be identified and tracked, such as the radar signals corresponding to the respiratory-related movements of the non-primary person 211. As described herein, the monitoring device 200 performs operations to target the respiratory-related data of the primary user 212 by identifying one or more time periods when the primary user 212 is not in the bed 250. In an embodiment, the monitoring device 200 removes respiratory-related data associated with the non-primary person 212 that is collected during the time period when the primary user 212 is out of the bed 250.

As illustrated in FIG. 2, the monitoring device 200 can identify a primary respiratory zone 213 and an out-of-bed zone 214 associated with a sleeping environment (e.g., bed 250) of a primary user 212. As shown, the detection zone 210 includes at least a portion that corresponds to a typical sleeping position of the non-primary person 211 (a person who sleeps in bed 250 with the primary user 212). In an embodiment, the detection zone 210 is an area or region that is monitored by one or more radar sensors of the monitoring device 200 to detect a set of radar signals associated with first respiratory-related movements of a primary user 212 and second respiratory-related movements of a second person 211 located within the detection zone 210 during a sleep session. In an embodiment, a sleep session is a period of time during which the primary user is engaged in sleep activity in a sleeping environment (e.g., the bed) in the detection zone for at least a portion of the time. In an embodiment, the monitoring device 200 is positioned or located on a side of the bed associated with the primary user 212 (e.g., to the side of the bed that the primary user occupies when going to sleep).

In an embodiment, the monitoring device 200 establishes or generates the out-of-bed zone 214 in a region adjacent to a side edge 215 of the bed 250 corresponding to a side of the bed 250 typically occupied by the primary user 212 during a sleep session. In an embodiment, the out-of-bed zone 214 is region adjacent to the bed that is identified relative to a primary respiratory zone 213 associated with the primary user 212. In an embodiment, the out-of-bed zone 214 includes a region between a first boundary axis 215 and a second boundary axis 216 identified in accordance with the processes described below with reference to FIGS. 3-5 (wherein FIGS. 3, 4A, and 4B relate to a first approach to generating the out-of-bed zone 213 and FIG. 5 relates to a second approach to generating the out-of-bed zone 213.

In an embodiment, the monitoring device 200 (e.g., out-of-bed zone motion tracker 106 of the monitoring device 100 of FIG. 1) monitors and tracks motion associated with the out-of-bed zone 214 to detect one or more time periods when the primary user 212 is not present in the bed 250. In an embodiment, the monitoring device 200 uses motion detection processing to determine when motion associated with the primary user 212 is detected within the out-of-bed zone 214 (e.g., when the primary user 212 moves from a sleeping position in the bed 250 and moves within the out-of-bed zone 214). In an embodiment, an out-of-bed zone event is identified in response to the first motion 220 shown in FIG. 2.

In an embodiment, the monitoring device 200 identifies and stores data corresponding to the first motion 220 detected in the out-of-bed zone 214 including a timestamp denoting a first time associated with the first motion 220. In an embodiment, the first time can be associated with a peak amplitude of a first distribution of radar signals detected within the out-of-bed zone 214. In an embodiment, the monitoring device 200 further identifies and stores data corresponding to the second motion 221 detected in the out-of-bed zone 214. In an embodiment, the second time can be associated with a peak amplitude of a second distribution of radar signals detected within the out-of-bed zone 214.

In an embodiment, a first timestamp associated with a peak amplitude of radar signals corresponding to motion 220 is identified and stored by the monitoring device 200. The monitoring device 200 further identifies and stores a second timestamp associated with a peak amplitude of radar signals corresponding to motion 221. The monitoring device 200 identifies a period of time between the first timestamp and the second timestamp when the primary user 212 was out of the bed 250 (the "out-of-bed period"). In an embodiment, the monitoring device 200 identifies a set or portion of respiratory data that was collected during the out-of-bed period (e.g., the respiratory-related data relating to the non-primary person 211 and noisy radar signals that are collected when the primary user 212 is out of the bed 250) and removes that portion of the respiratory-related data from the set of data collected during a sleep session. By removing the respiratory-related data collected during the identified time period when it is detected that the primary user 212 is out of the bed 250, a final set of respiratory-related data is identified that corresponds to the primary user 212 only.

Figure 3:
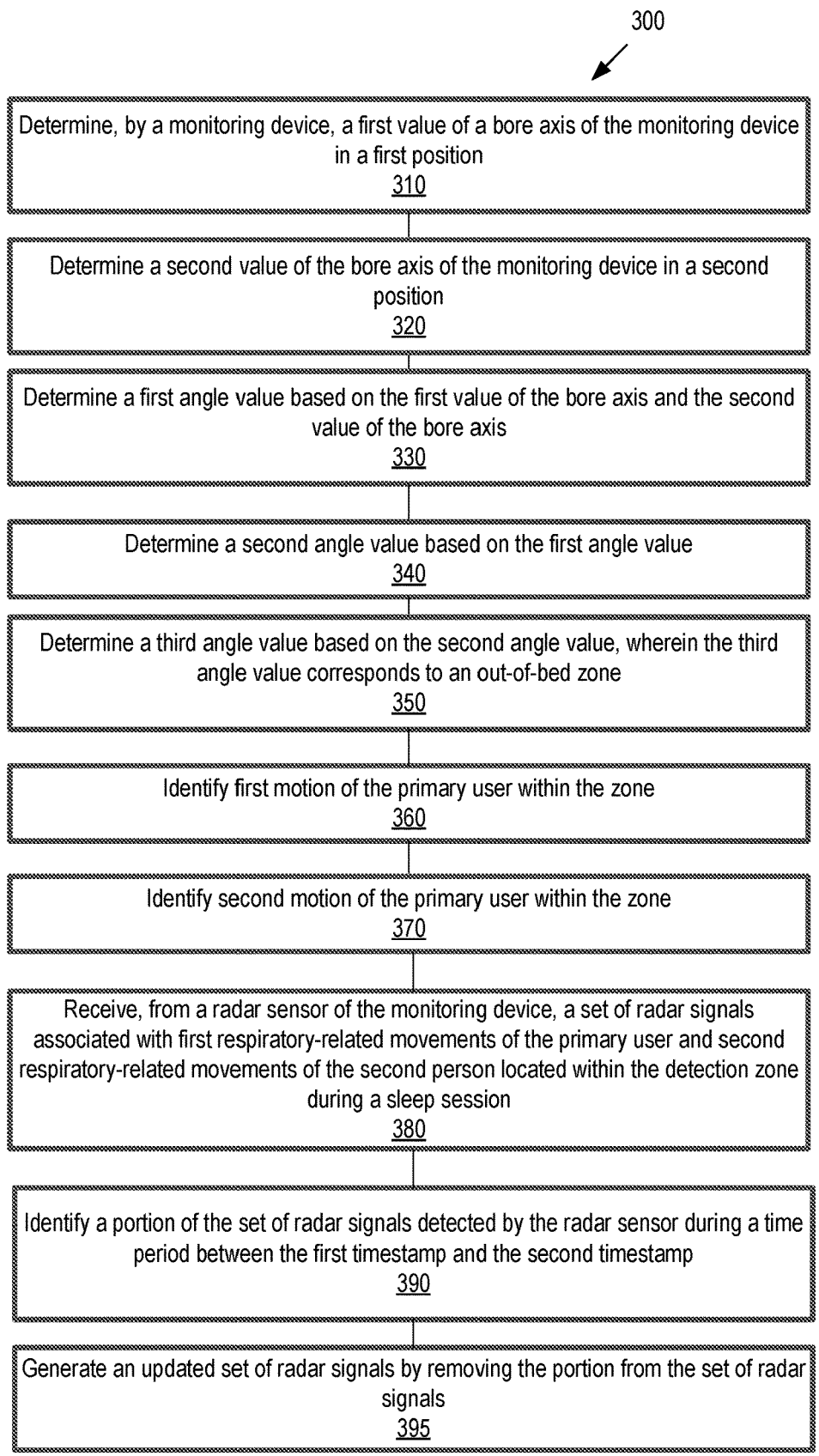
FIG. 3 is an exemplary flow diagram of a method for generating and monitoring an out-of-bed zone associated with a sleeping environment to identify out-of-bed zone entry and exit events, according to one or more embodiments.

According to embodiments of the present disclosure, the monitoring device (e.g., monitoring device 100 of FIG. 1 and monitoring device 200 of FIG. 2) identifies the primary respiratory zone 213 and the out-of-bed zone 214 shown in FIG. 2 according to an example method 300 shown in FIG. 3.

FIG. 3 is a flow diagram of an example method 300 for determining a primary respiratory zone and an out-of-bed zone associated with a detection zone including the sleeping environment of the primary user, according to embodiments of the present disclosure. The method 300 of FIG. 3 is executed to identify a first boundary axis and a second boundary axis of the out-of-bed zone relative to a primary respiratory zone, wherein the out-of-bed zone is a region between the first boundary axis and the second boundary axis. It is understood that the flowchart of FIG. 3 provides an example of the many different types of functional arrangements that may be employed to implement the operation of a monitoring device as described herein.

The method 300 of FIG. 3 may be performed by processing logic of a monitoring device (e.g., detection zone manager 104 of monitoring device 100 of FIG. 1) that comprises hardware (e.g., circuitry, dedicated logic, programmable logic, microcode, etc.), software (e.g., instructions run on a processing device to perform hardware simulation), or a combination thereof. In an embodiment, certain functions and activities may be performed by a remote computing system connected to a monitoring device via a suitable network. The operations of method 300 may be performed in any order so as to fit the needs of the functionality to be provided.

In block 310, the processing logic of a monitoring device determines a first value of a bore axis of the monitoring device in a first position. In an embodiment, during a setup phase, the monitoring device is arranged in the first position. In the first position, a front of the monitoring device is substantially parallel to a side or edge of a bed associated with the primary user. In the first position, a bore axis of the monitoring device is in an at least substantially perpendicular alignment relative to an edge of the side of the bed. In the first position, with the bore axis in perpendicular alignment with the edge of the side of the bed, the monitoring device determines a first value of the bore axis (i.e., the reference value). In an embodiment, the reference value corresponding to the bore axis of the monitoring device in the first position is represented as a 0° azimuth angle.

FIG. 4A illustrates a monitoring device 400 in accordance with method 300 in an example position next to a side of the bed 450. In the example shown, the monitoring device 400 is positioned on a same side (e.g., the right-side in FIG. 4A) as the side of the bed 450 occupied by the primary user (e.g., the person targeted for respiratory activity tracking). In the example shown, the left-side of the bed 450 can be occupied by a non-primary person (e.g., the second person that is not targeted for respiratory activity tracking).

As shown in FIG. 4A, the first position of the monitoring device 400 is next to the primary user's side of the bed 450 and oriented such that a face or front of the monitoring device 401 is parallel to an edge 451 of the bed 450. In an embodiment, the monitoring device can be arranged in the first position (with the front 451 facing and parallel to the edge 451 of the bed 450) during a setup stage associated with the monitoring device 400.

In an embodiment, in operation 310, the monitoring device determines the reference value 402 of a bore axis 403 of the monitoring device 400 in the first position. In an embodiment, the reference value is a baseline orientation value of the bore axis 403 of the monitoring device when in the first position. In an embodiment, the reference value 402 can be set as an azimuth angle value or a relative value (e.g., 0°) corresponding to the orientation of the monitoring device in the first position.

In an embodiment, the monitoring device is rotated (e.g., by the primary user during the setup phase) from the first position to a second position. In the second position, a bore axis of the monitoring device is aligned with a primary respiratory zone of the detection zone. For example, during a guided setup routine, having established the reference value 402, the primary user can be prompted to rotate the monitoring device to align the bore axis of the device with a location within the bed corresponding to where the primary user's chest (i.e., the primary respiratory zone) is positioned with the primary user is in the lying position.

In operation 320, the processing logic determines a second value of the bore axis of the monitoring device in a second position. In an embodiment, the monitoring device is rotated from the first position (used during operation 310) to the second position and one or more sensors of the monitoring device determine the angular rotation of the monitoring device when rotated from the first position to the second position.

In an embodiment, the monitoring device is rotated (e.g., by the primary user during the setup phase) from the first position to a second position. In the second position, a bore axis of the monitoring device is at least substantially aligned with a primary respiratory zone of the detection zone. For example, during a guided setup routine, having established the reference value, the primary user can be prompted to rotate the monitoring device to align the bore axis of the device with a location within the bed corresponding to where the primary user's chest (i.e., the primary respiratory zone) is positioned with the primary user is in the lying position or typical sleeping position. In an embodiment, based on an input from the user (e.g., the rotation of the monitoring device), in the second position, the monitoring device approximates the primary respiratory zone of the primary user by aligning the bore axis of the monitoring device with an approximate location of the primary user's chest when in the sleeping position. As shown in FIG. 4B, the monitoring device 400 is rotated to a second position where the bore axis 403 aligns with a primary respiratory zone of the primary user 412 when in a sleeping position within the bed 450.

In operation 330, the processing logic determines a first angle value based on the first value of the bore axis and the second value of the bore axis. In an embodiment, the first angle value corresponds to an arc length between the bore axis in the first position (e.g., a first side) and the bore axis in the second position. In an embodiment, one or more sensors (e.g., IMU sensors, magnetometer sensors, etc.) of the monitoring device calculate the first angle value by measuring the angular rotation of the monitoring device when rotated from the first position (e.g., when the bore axis of the monitoring device is in a substantially perpendicular alignment with the edge of the side of the bed) to the second position (e.g., when the bore axis of the monitoring device is in substantial alignment with the primary respiratory zone of the primary user).

As shown in FIG. 4B, the first angle value is an arc length between the first value of the bore axis (i.e., reference value 402) to the second value of the bore axis 404 (i.e., in alignment with the primary respiratory zone of the primary user 412). In an embodiment, the measured rotation of the monitoring device corresponding to rotation from the first position to the second position can be used to determine the first angle value, where the first angle value corresponds to a first angle (e.g., angle A in FIG. 4B) formed by the bore axis in the first position and the bore axis in the second position diverging from a common vertex point (e.g., the monitoring device in the second position). In the example shown in FIG. 4B, an example range of the first angle (A) can be approximately −10° to −55° relative to the 0° reference value 402.

In operation 340, the processing device determines a second angle value based on the first angle value. In an embodiment, the second angle value is an arc length determined by calculating a difference between a right angle value (i.e., a 90° angle value) and the first angle value. In an embodiment, a position of a first boundary axis of the out-of-bed zone is determined by spanning the second angle value from the bore axis when the monitoring device is in the second position (e.g., in alignment with the primary respiratory zone). In an embodiment, a second angle having the second angle value is formed between the bore axis of the monitoring device in the second position and the first boundary axis.

In an embodiment, as shown in FIG. 4B, the second angle (angle B) is calculated by determining a difference between a right angle value (e.g., 90°) of the monitoring device in the second position relative to the first angle (angle B). As shown in FIG. 4B, a position of a first boundary axis 415 of an out-of-bed zone 414 is determined by spanning the second angle value (e.g., the value of angle B) from the bore axis 404 when the monitoring device is in the second position (e.g., in alignment with the primary respiratory zone).

As shown in FIG. 4B, the second angle (angle B) is an angle spanning from the bore axis 404 of the monitoring device in the second position to the first boundary axis 415 of the out-of-bed zone next to the side of the bed. In an embodiment, angle B is calculated by determining a difference between 90° and the absolute value of angle A, as represented by the following expression:

$$\text{Angle } B = 90° - |\text{Angle } A|$$

In operation 350, the processing device calculates a third angle value based on the second angle value, wherein the third angle value corresponds to an out-of-bed zone. In an embodiment, the third angle value corresponds to a third angle formed by the first boundary axis and a second boundary axis diverging from a common vertex point (e.g., the monitoring device in the second position). In an embodiment, the third angle value is an arc length spanning from the first boundary axis of the out-of-bed zone to a second boundary axis of the out-of-bed zone. In an embodiment, the third angle value of the third angle is determined by spanning an offset arc length (e.g., 20° to 90°) from the position of the first boundary axis. In an embodiment, the third angle corresponds to the out-of-bed zone that is monitored by the monitoring device to detect motion.

As shown in FIG. 4B, the third angle (angle C) is formed by the first boundary axis 415 and the second boundary axis 416 diverging from the monitoring device 400 in the second position. In an embodiment, the third angle (angle C) corresponds to the out-of-bed zone 414. In an embodiment, the out-of-bed zone 414 is a region extending between the first boundary 415 to a second boundary 416 of the out-of-bed zone 414, as defined by the third angle (angle C). In the example shown, the second boundary 416 of the out-of-bed zone 414 can be established by spanning an offset angle value (e.g., −20° to)−90° from the first boundary axis 415. In an embodiment, the angle between the first boundary 415 and the second boundary 416 (labeled as angle "C" in FIG. 4B) is established by adding an offset angle (e.g., 20° and 90°) to the angle of the first boundary 415 (e.g., angle "B"). In an embodiment, the out-of-bed zone includes a region between the first boundary 415 and the second boundary 416 as defined by the corresponding angles of the respective boundaries, as described above.

In operation 360 of FIG. 3, the processing device identifies first motion of the primary user within the out-of-bed zone. In an embodiment, the processing device detects when the primary user is moving within the out-of-bed zone by identifying a distribution of radar signals associated with the out-of-bed zone. In an embodiment, the processing logic identifies a first time corresponding to a first peak amplitude of a distribution of radar signals associated with motion by an object within the out-of-bed zone. In an embodiment, the processing logic generates a first timestamp corresponding to the first time.

In operation 370, the processing device identifies second motion of the primary user with the zone (i.e., the out-of-bed zone). As described above, in an embodiment, the processing device detects when the primary user is moving within the out-of-bed zone by identifying a further distribution of radar signals associated with the out-of-bed zone. In an embodiment, the processing logic identifies a second time corresponding to a second peak amplitude of a second distribution of radar signals associated with second motion by an object within the out-of-bed zone (e.g., the motion of the object as he or she moves through the zone while returning to the bed). In an embodiment, the processing logic generates a second timestamp corresponding to the second time.

In operation 380, the processing logic receives, from a radar sensor of the monitoring device, a set of radar signals associated with first respiratory-related movements of the primary user and second respiratory-related movements of a second person located within the detection zone during a sleep session. In an embodiment, the radar sensor detects respiratory-related movements (e.g., movements of the chest associated with breathing) of the primary user when the primary user is in the typical sleeping position with his or her chest substantially within the primary respiratory zone. In an embodiment, in the event the primary user exits the bed, the radar sensor switches to detecting the second respiratory-related movements of the second person in the detection zone.

In operation 390, the processing logic identifying a portion of the set of radar signals detected by the radar sensor during a time period between the first timestamp and the second timestamp. As noted above, when the primary user is out of the bed (e.g., during the time period between the first time and the second time), the portion of the set of radar signals corresponds to the respiratory-related movements of the second person. Advantageously, using the timestamp information relating to the period of time when the primary user is out of the bed (as indicated by the detected motion within the out-of-bed zone), the processing device can identify the portion of the overall or total radar signals detected during the sleep session that correspond to the second person or represent noise, as opposed to respiratory-related movements of the primary user.

In operation 395, the processing logic generates an updated set of radar signals by removing the portion from the set of radar signals. In an embodiment, by removing the portion of radar signals detected during the time period when the primary user is out of the bed, the updated set of radar signals is filtered to include those signals associated with the respiratory-related movements of the primary user. Advantageously, the updated set of radar signals, targeting the primary user, can be used for further processing to generate one or more sleep-related analytics associated with the primary user (e.g., a sleep score).

In an embodiment, the time period between the first timestamp and the second timestamp when the primary user is determined to be out of the bed is identified. The time period (also referred to as the out-of-bed time period) is maintained and used in connection with the respiratory activity monitoring. In an embodiment, the set of respiratory activity data for a sleep session is adjusted or updated to remove or exclude a subset of the respiratory activity data that occurred during the out-of-bed time period. In an embodiment, the respiratory data collected during the out-of-bed time period represents false-positive data since the primary user was not in the bed and aligned with the primary respiratory zone as indicated by the out-of-bed zone entry and exit indicators.

Figure 5:
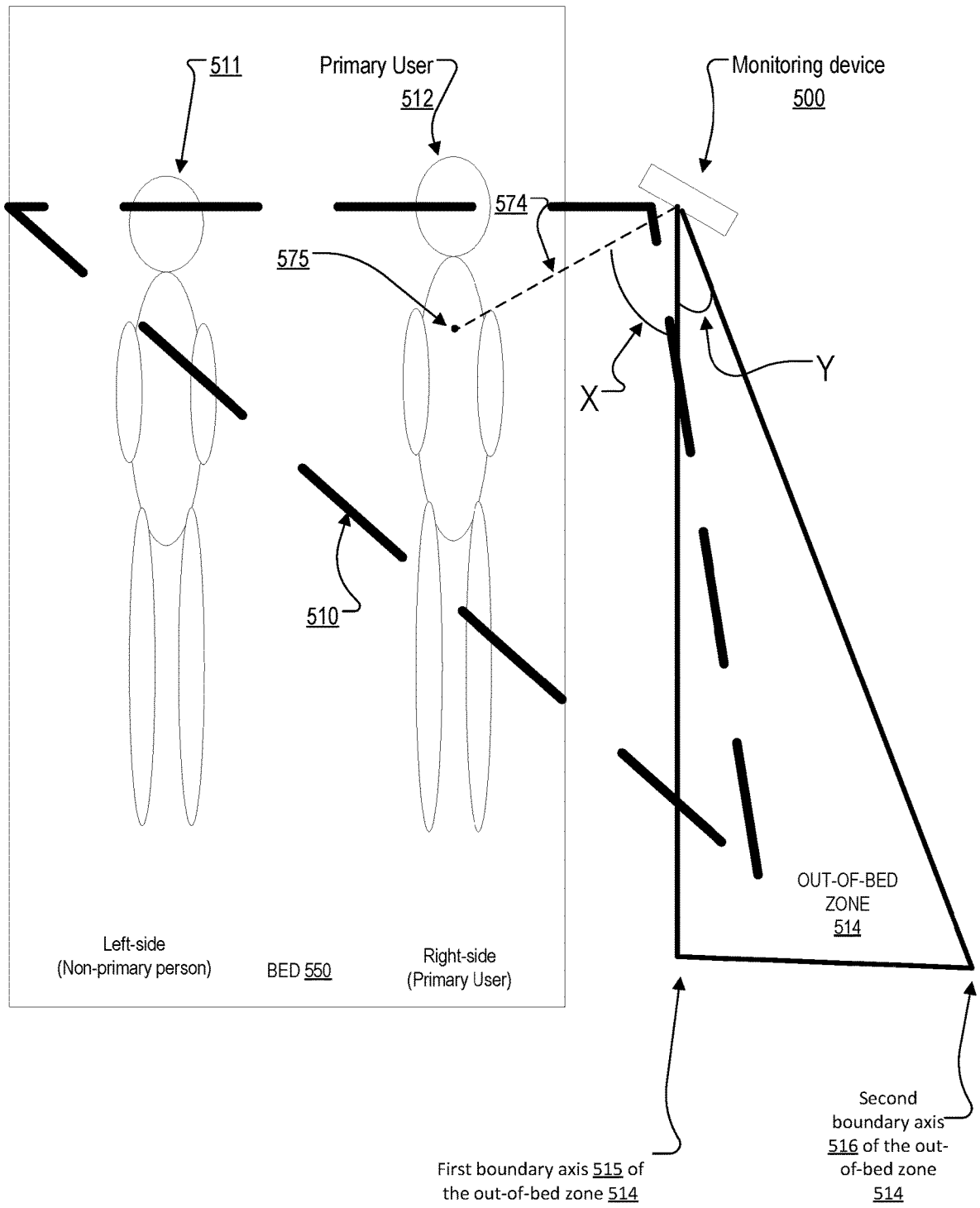
FIG. 5 illustrates an example of generating and monitoring an out-of-bed zone associated with a sleeping environment to identify out-of-bed zone motion detection data, according to one or more embodiments.

FIG. 5 illustrates another embodiment relating to the generation of an out-of-bed zone 514 identified and monitored by a monitoring device 500. In this embodiment, during a setup phase of the monitoring device 500, a user can provide an indication of which side of the bed 550 (e.g., by providing an input to a prompt during a setup routine) the monitoring device 500 is located (e.g., the right-side of the bed 550 in the example of FIG. 5). During use of the monitoring device 500 to monitor respiratory activity within the detection zone 510, a primary respiratory zone associated with a primary user 512 is identified.

In an example, the primary respiratory zone can be identified based on an analysis of a set of historical radar signals associated with respiratory-related movements of the primary user. In an embodiment, the monitoring device is positioned next to a side of the bed associated with the primary user. Over a period of time, the monitoring device collects respiratory-related radar signals from the detection zone. In an embodiment, the primary respiratory zone is associated with a location within the detection zone that corresponds to a subset of radar signals having a highest relative signal strength of the set of radar signals. In an embodiment, a voxel mapping is performed using the historical radar signals to identify one or more voxels within the detection zone that correspond to the subset of the radar signals having the highest relative signal strength. In an embodiment, a centroid of a voxel associated with the location of the subset of radar signals can be identified.

In an embodiment, the processing logic identifies a long term average of an azimuth angle (relative to the monitoring device in a position during collection of the historical radar signal set) with respect to one or more voxel centroids identified over time (e.g., multiple sleep sessions) representing the highest strength radar signals of multiple sets of radar data. In an embodiment, the long term average of the azimuth angle corresponds to a location (e.g., location 575) within the detection zone. In an embodiment, the location 575 represents a position or location of the primary respiratory zone. In an embodiment, the radar data can include imaging radar signals corresponding to respiration motion in a 3D space corresponding to the detection zone 510) to enable the identification of the primary respiratory zone (e.g., a location in the sleeping environment corresponding to a set of respiration signals collected over a period of time that have a highest relative signal strength as determined by the one or more radar sensors of the monitoring device 500).

In an example, the voxel mapping of respiratory-related radar signals is analyzed to determine an axis line (e.g., axis 574 of FIG. 5) corresponding to an approximate centroid of the voxel mapping associated with the subset of radar signals (e.g., location 575). In an embodiment, a long term average of multiple axis lines aligned with centroid values of collected radar data (e.g., imaging radar configured to locate respiration motion in a 3D space corresponding to the detection zone) is determined and used to identify or approximate a location representing the primary respiratory zone.

In an embodiment, as the primary user breaths, his or her whole body can move periodically in accordance with the breathing pattern. In an embodiment, the voxel selected for respiration waveform extraction can correspond to some part of the body. With a long enough observation time, the distribution of the coordinates of the voxels depict a contour of the human body and the primary respiratory zone can be determined accordingly. In an embodiment, the average azimuth angle of these voxels substantially point to the chest of the primary user, since the chest motion has the largest amplitude compared with other parts of the body.

In this embodiment, a first angle (e.g., angle X in FIG. 5) diverging from the monitoring device 500 is determined by spanning a first offset angle value from the axis 574 of the monitoring device 500 aligned with a location 575 associated with the primary respiratory zone (e.g., in view of the indication of the side of the bed the monitoring device is located). The angle X has an angle value corresponding to an arc length between the line 574 corresponding to the primary respiratory zone 574 and a first boundary axis 515 of an out-of-bed zone 514. In an embodiment, the first angle (angle X) is formed by the line corresponding to the primary respiratory zone 574 and the first boundary axis 515 diverging from a common vertex point (e.g., the monitoring device 500). In an embodiment, a first angle value of the first angle is determined by spanning a first offset angle value from the line 574 corresponding to the primary respiratory zone.

In an embodiment, the offset angle value can be an angle value in a predetermined range of angles (e.g., 20° to 45°) and be based on the side of the bed associated with the primary user 512 identified during a setup or initialization phase.

In an embodiment, a second angle (angle Y in FIG. 5) is determined based on the first boundary axis 516. In an embodiment, the second angle (angle Y) corresponds to the out-of-bed zone 514, wherein the out-of-bed zone 514 is a region between the first boundary axis 515 and the secondary boundary axis 516. In an embodiment, a second angle value of the second angle is determined by spanning a second offset angle value (e.g., 20° to 90°) from the first boundary axis 515.

As described above, the dynamically generated out-of-bed zone 514 is monitored to identify out-of-bed zone entry and exit events to enable the identification of out-of-bed activity by the primary user 512. The out-of-bed activity can be identified by a first timestamp (e.g., a first time when the primary user 512 crosses the first boundary of the out-of-bed zone 514 and enters the out-of-bed zone 514) and a second timestamp (e.g., a second time when the primary user 512 crosses the first boundary 515 of the out-of-bed zone 514 as he or she re-enters the bed 550). The first timestamp and ending timestamp define a time period when the primary user 512 is identified as out-of-the-bed. In an embodiment, radar signals collected by the one or more radar sensors of the monitoring device 500 during the identified time period (e.g., respiratory data relating to movement by the non-primary user 513) can be removed, ignored, or excluded from the overall respiratory data corresponding to the sleep session of the primary user 512.

Figure 6:
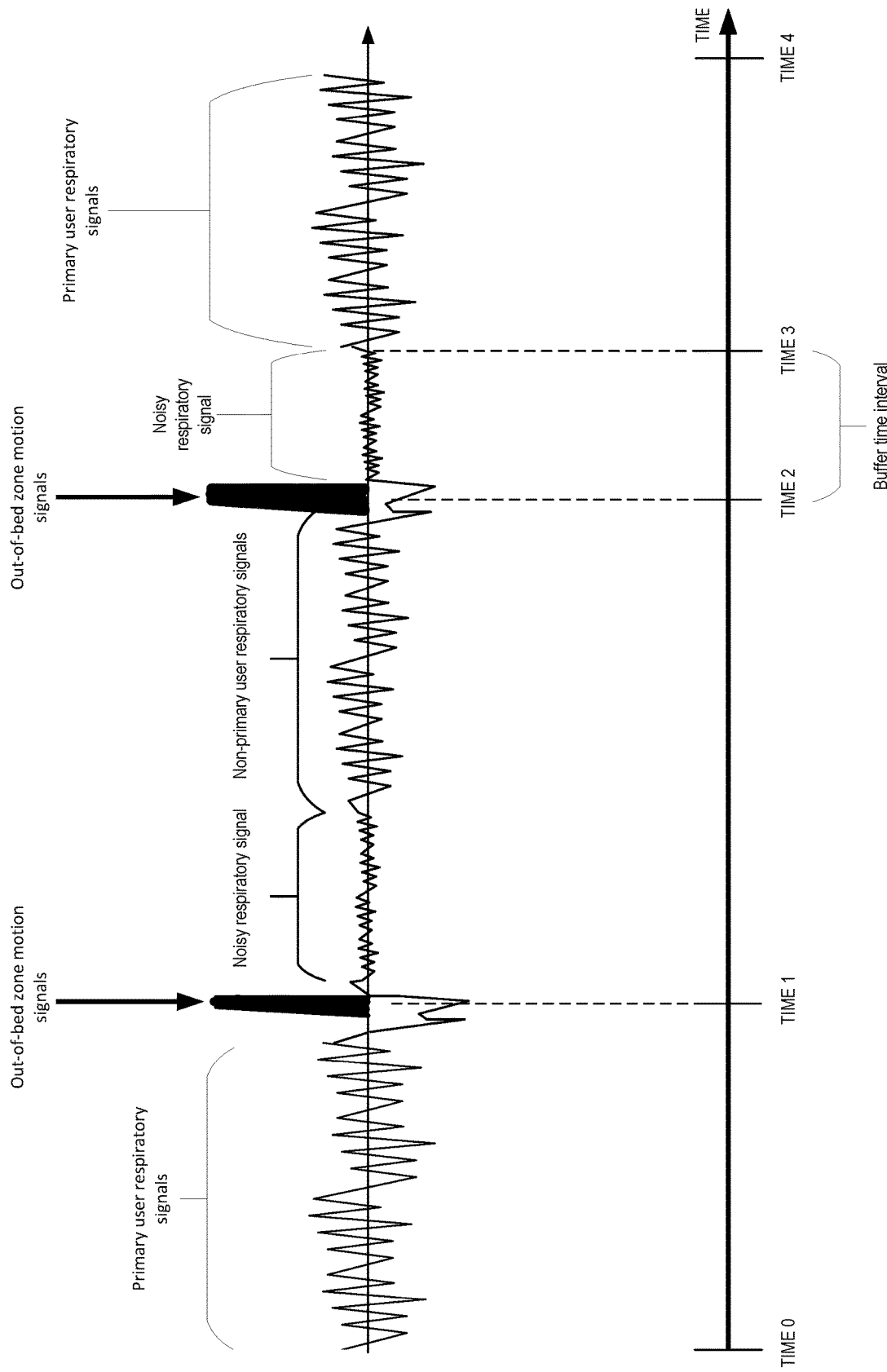
FIG. 6 illustrates an example overlay of radar signal data corresponding to a radar spectrum including respiratory-related radar signals and motion-related radar signals associated with an out-of-bed zone collected by a monitoring device according to embodiments of the present disclosure.

FIG. 6 illustrates an example overlay of radar signals corresponding to a radar spectrum including respiratory-related radar signals and motion-related radar signals (represented in solid lines) associated with an out-of-bed zone collected over a time period (e.g., Time 0 to Time 4) by a monitoring device according to embodiments of the present disclosure. As shown in FIG. 6, during a first time period (e.g., from Time 0 to Time 1), the monitoring device detects a first set of respiratory-related radar signals corresponding to a bed including a primary user and a non-primary user. In an embodiment, as described above, the monitoring device is positioned next to a side of the bed that is occupied by the primary user. During the first time period, the strongest and closest respiratory-related radar signals collected from the bed area are associated with the primary user.

As shown in FIG. 6, in response to the primary user exiting the bed and entering the out-of-bed zone, the monitoring device detects a first set of out-of-bed motion signals. As shown in FIG. 6, a peak amplitude of a first distribution of radar signals associated with the motion within the out-of-bed zone is identified at Time 1. In an embodiment, the monitoring device identifies and stores a timestamp identifying Time 1 associated with first motion of the primary user within the out-of-bed zone. As shown in FIG. 6, starting from Time 1, since the primary user is out of the bed (as indicated by the detected motion within the out-of-bed zone), the monitoring device detects a first set of noisy respiratory-related radar signals and a first set of respiratory-related radar signals associated with the non-primary user.

In the example shown, in response to the primary user re-entering the out-of-bed zone as he or she returns to the bed, the monitoring device detects a second set of out-of-bed motion signals. As shown in FIG. 6, a peak amplitude of a second distribution of radar signals associated with the motion within the out-of-bed zone is identified at Time 2. In an embodiment, the monitoring device identifies and stores a timestamp identifying Time 2 associated with second motion of the primary user within the out-of-bed zone.

In an embodiment, noisy respiratory signals may be collected during a buffer time interval following the time associated with the primary user returning to the bed (e.g., a buffer time interval between Time 2 and Time 3, as shown in FIG. 6). In an embodiment, in response to the primary user returning to the bed and his or her sleeping position, the monitoring device collects a next set of primary respiratory signals associated with the primary user (e.g., the set of signals corresponding to the time period between Time 3 and Time 4).

In an embodiment, using the timestamp information associated with the first motion of the primary user within the out-of-bed zone and the second motion of the primary user within the out-of-bed zone, a time period is identified that corresponds with the primary user being of the bed (i.e., the out-of-bed period). In this example, the monitoring device can identify a subset of the overall respiratory signals (e.g., respiratory-related radar signals collected from Time 0 to Time 4) collected during a time period between Time 1 and Time 2. In an embodiment, the subset of respiratory-related signals collected between Time 1 and Time 2 can be identified and removed from the overall set of respiratory-related radar signals since it relates to time period when the primary user was determined to be out of the bed.

In an embodiment, the monitoring device can further identify a buffer time interval following the second motion within the out-of-bed zone (e.g., a time period between Time 2 and Time 3). In an embodiment, the monitoring device can identify a subset of respiratory-related radar signals collected during the buffer time interval as a noisy signal set (e.g., signals that are not related to the respiratory-related movements of the primary user) that is to be removed from the overall respiratory-related data collected during the sleep session (e.g., a time between Time 0 and Time 4). Advantageously, detecting the out-of-bed zone motion signals at Time 1 and Time 2 enables the identification of respiratory signals collected during a period between those times to improve the targeting of respiratory signals associated with the primary user.

Figure 7:
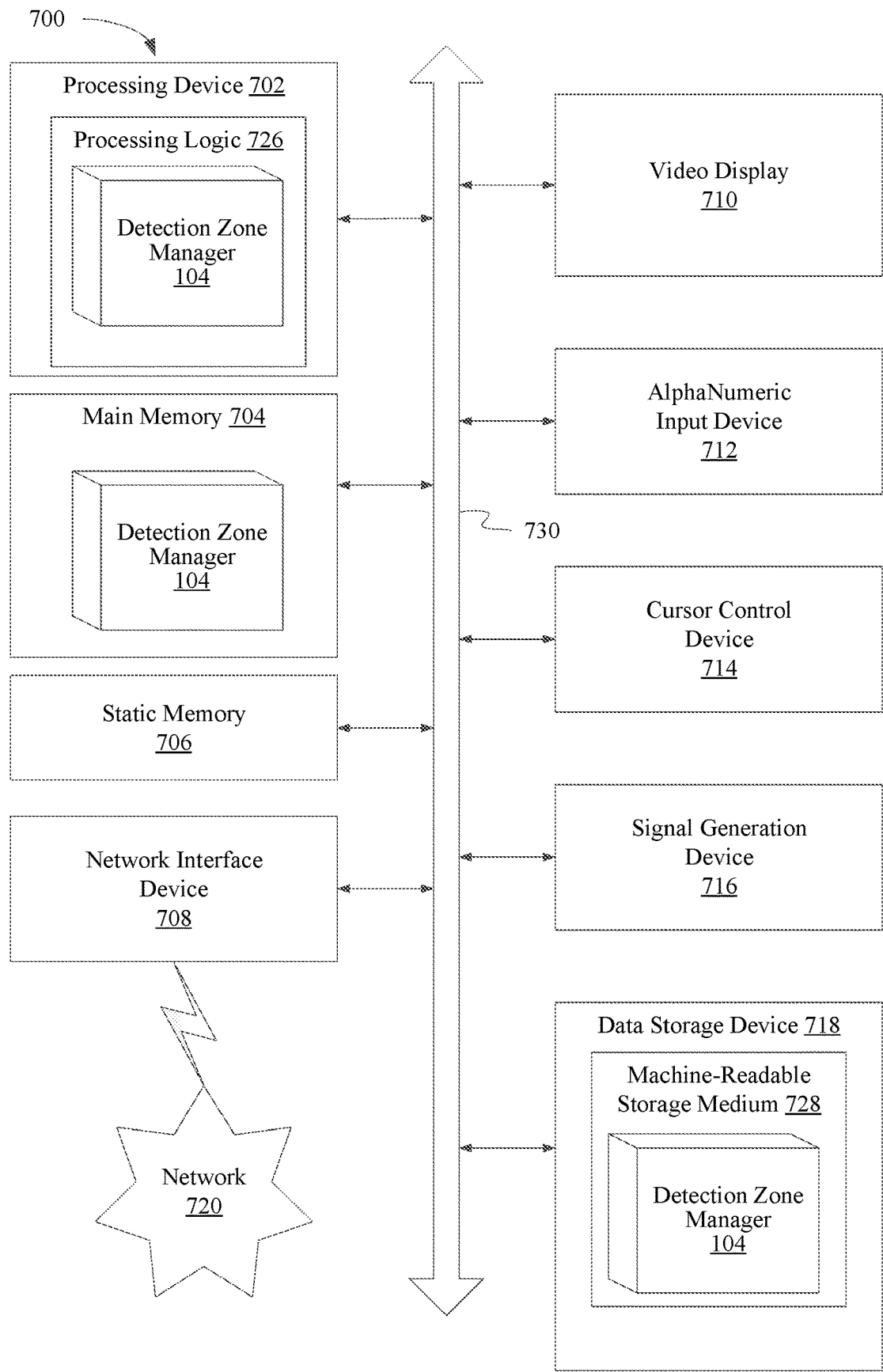
FIG. 7 illustrates a diagrammatic representation of a machine in the example form of a computer system including a set of instructions executable by a computer to manage connectivity of a client device in a mesh network, according to one or more embodiments.

FIG. 7 illustrates a diagrammatic representation of a machine in the example form of a computer system 700 including a set of instructions executable by a computer to manage connectivity of a client device in a mesh network based on synchronized connection cost metrics associated with multiple connection paths according to any one or more of the methodologies discussed herein. In one embodiment, the computer may include instructions to enable execution of the processes and corresponding components shown and described in connection with FIGS. 1-4.

In alternative embodiments, the machine may be connected (e.g., networked) to other machines in a LAN, an intranet, an extranet, or the Internet. The machine may operate in the capacity of a server machine in a client-server network environment. The machine may be a personal computer (PC), a set-top box (STB), a server, a network router, switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein The example computer system 700 includes a processing device (processor) 702, a main memory 704 (e.g., read-only memory (ROM), flash memory, dynamic random access memory (DRAM) such as synchronous DRAM (SDRAM)), a static memory 706 (e.g., flash memory, static random access memory (SRAM)), and a data storage device 718, which communicate with each other via a bus 730.

Processing device 702 represents one or more general-purpose processing devices such as a microprocessor, central processing unit, or the like. More particularly, the processing device 702 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 702 may also be one or more special-purpose processing devices such as an application specific integrated circuit (ASIC), a field programmable gate array (FPGA), a digital signal processor (DSP), network processor, or the like. In various implementations of the present disclosure, the processing device 702 is configured to execute instructions for the detection zone manager 104 performing the operations and processes described herein.

The computer system 700 may further include a network interface device 708. The computer system 700 also may include a video display unit 710 (e.g., a liquid crystal display (LCD) or a cathode ray tube (CRT)), an alphanumeric input device 712 (e.g., a keyboard), a cursor control device 714 (e.g., a mouse), and a signal generation device 716 (e.g., a speaker).

The data storage device 718 may include a computer-readable storage medium 728 (or machine-readable medium) on which is stored one or more sets of instructions of the detection zone manager 104 embodying any one or more of the methodologies or functions described herein. The instructions may also reside, completely or at least partially, within the main memory 704 and/or within processing logic 726 of the processing device 702 during execution thereof by the computer system 700, the main memory 704 and the processing device 702 also constituting computer-readable media.

The instructions may further be transmitted or received over a network 720 via the network interface device 708. While the computer-readable storage medium 728 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely presented as examples. Particular implementations may vary from these example details and still be contemplated to be within the scope of the present disclosure. In the above description, numerous details are set forth.

It will be apparent, however, to one of ordinary skill in the art having the benefit of this disclosure, that embodiments of the disclosure may be practiced without these specific details. In some instances, well-known structures and devices are shown in block diagram form, rather than in detail, in order to avoid obscuring the description.

Some portions of the detailed description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to the desired result. The steps are those requiring physical manipulations of physical quantities. Usually, though not necessarily, these quantities take the form of electrical, magnetic, or optical signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as: detecting", "identifying", "determining", or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

Embodiments of the disclosure also relate to an apparatus for performing the operations herein. This apparatus may be specially constructed for the required purposes, or it may comprise a general purpose computer selectively activated or reconfigured by a computer program stored in the computer. Such a computer program may be stored in a computer-readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions.

The algorithms and displays presented herein are not inherently related to any particular computer or other apparatus. Various general-purpose systems may be used with programs in accordance with the teachings herein, or it may prove convenient to construct a more specialized apparatus to perform the required method steps. The required structure for a variety of these systems will appear from the description below. In addition, the present embodiments are not described with reference to any particular programming language. It will be appreciated that a variety of programming languages may be used to implement the teachings of the present disclosure as described herein. It should also be noted that the terms "when" or the phrase "in response to," as used herein, should be understood to indicate that there may be intervening time, intervening events, or both before the identified operation is performed.

It is to be understood that the above description is intended to be illustrative, and not restrictive. Many other embodiments will be apparent to those of skill in the art upon reading and understanding the above description. The scope of the disclosure should, therefore, be determined with reference to the appended claims, along with the full scope of equivalents to which such claims are entitled.

What is claimed is:

1. A monitoring device comprising:
a radar sensor;
a processing device coupled to the radar sensor; and
a memory coupled to the processing device storing computer-executable instructions that, when executed, cause the processing device to perform operations comprising:
detecting, by the radar sensor, a first set of radar signals associated with respiratory movements of at least one of a first user and a second user within a first zone comprising at least a portion of a bed;
detecting, by the radar sensor at a first time, a second set of radar signals associated with first motion of the first user in a second zone located adjacent to a first side of the bed;
detecting, by the radar sensor at a second time, a third set of radar signals associated with second motion of the first user in the second zone located adjacent to the first side of the bed;
identifying a portion of the first set of radar signals corresponding to a time period between the first time and the second time;
generating a modified first set of radar signals by removing the portion of the first set of radar signals from the first set of radar signals; and
causing generation of a sleep-related analytic associated with the first user using the modified first set of radar signals.

2. The monitoring device of claim 1, wherein the operations further comprise:
determining a first value representing an orientation of a bore axis of the monitoring device in a first position;
determining a second value representing the orientation of the bore axis of the monitoring device in a second position;
determining a first angle value of the monitoring device in the second position using the first value and the second value;
determining a second angle value based on the first angle value, wherein the second angle value is a difference between a right angle value and the first angle value; and
determining a third angle value based on the second value of the bore axis of the monitoring device, the second angle value, and an offset angle value, wherein the third angle value corresponds to the second zone.

3. The monitoring device of claim 1, wherein the operations further comprise:
determining a first value representing an orientation of a bore axis of the monitoring device in a first position, wherein the bore axis of the monitoring device in the first position is substantially perpendicular to the first side of the bed;
determining a second value representing the orientation of the bore axis of the monitoring device in a second position, wherein the bore axis of the monitoring device in the second position is substantially aligned with a location within the first zone corresponding to a respiratory zone of the first user when in a sleeping position;

determining a first angle diverging from the radar sensor of the monitoring device in the second position using the first value and the second value, wherein the first angle corresponds to an angular rotation of the monitoring device from the first position to the second position;

determining a second angle diverging from the radar sensor of the monitoring device in the second position using the first angle and a third value representing a perpendicular axis of the bore axis of the monitoring device in the first position, wherein the third value defines a first boundary axis of the second zone; and determining a third angle diverging from the radar sensor of the monitoring device in the second position using the third value and a fourth value representing an offset angle from the perpendicular axis of the bore axis of the monitoring device in the first position, wherein the fourth value defines a second boundary axis of the second zone, wherein the second zone comprises a region between the first boundary axis and the second boundary axis.

4. The monitoring device of claim 1, wherein the operations further comprise:

identifying a location within the first zone, the first zone being associated with a respiratory zone of the first user;

determining, based on an axis of the monitoring device aligned with the location and a first offset angle value, a first angle diverging from the monitoring device; and determining, based on the first angle and a second offset angle value, a second angle diverging from the radar sensor of the monitoring device, wherein the second angle corresponds to the second zone.

5. The monitoring device of claim 1, wherein the first zone is associated with a respiratory zone of the first user and the operations further comprise:

identifying a location within the first zone, wherein the location corresponds to a subset of radar signals having a highest relative signal strength of a historical radar signal set associated with the first zone;

determining a first angle diverging from the radar sensor of the monitoring device, wherein the first angle having a first angle value determined by adding a first offset angle value to a value representing an orientation of an axis of the monitoring device that is aligned with the location within the first zone associated with the respiratory zone; and determining a second angle diverging from the monitoring device, wherein the second angle having a second angle value determined by adding a second offset angle value to the first angle value, wherein the first angle value and the second angle value define the second zone.

6. The monitoring device of claim 1, wherein the operations further comprise:

determining a first value of a bore axis of the monitoring device in a first position, wherein a front of the monitoring device is substantially parallel with an edge of the first side of the bed;

determining that the monitoring device is in a second position;

measuring, by a sensor of the monitoring device in the second position, an angular rotation value between the first position and the second position;

determining a first angle value based on the angular rotation value;

determining a second angle value based on the first angle value, wherein the second angle value is a difference between a right angle value and the first angle value; and generating the second zone by adding an offset angle value to the second angle value.

7. The monitoring device of claim 1, wherein the operations further comprise:

determining an angle diverging from the radar sensor of the monitoring device in a position associated with detecting the first set of radar signals, wherein the angle is formed by a first boundary axis and a second boundary axis of the second zone.

8. A method comprising:

detecting, by a radar sensor of a monitoring device, a first set of radar signals associated with respiratory movements of at least one of a first user and a second user within a first zone comprising at least a portion of a bed;

generating a second zone adjacent to a first side of the bed, wherein the second zone corresponds to an angle diverging from the radar sensor of the monitoring device in a position when detecting the first set of radar signals;

detecting, by the radar sensor, a second set of radar signals associated with motion in the second zone;

detecting, by the radar sensor at a first time, a first subset of the second set of radar signals associated with first motion by the first user in the second zone;

detecting, by the radar sensor at a second time, a second subset of the second set of radar signals associated with second motion by the first user in the second zone; and identifying a portion of the first set of radar signals corresponding to a time period between the first time and the second time;

generating a modified first set of radar signals by removing the portion of the first set of radar signals from the first set of radar signals; and generating a sleep-related analytic associated with the first user using the modified first set of radar signals.

9. The method of claim 8, further comprising:

determining a first value of a bore axis of the monitoring device in a first position wherein the bore axis of the monitoring device is substantially perpendicular to the first side of the bed;

determining a second value of the bore axis of the monitoring device in a second position wherein the bore axis of the monitoring device is substantially aligned with a location within the first zone corresponding to a respiratory zone of the first user when in a sleeping position;

determining a first angle diverging from the radar sensor of the monitoring device in the second position, wherein the first angle has a first angle value corresponding to an angular rotation between the first value of the bore axis of the monitoring device in the first position and the second value of the bore axis of the monitoring device in the second position;

determining a second angle diverging from the radar sensor of the monitoring device in the second position, wherein the second angle is formed by the second value of the bore axis of the monitoring device in the second position and a first boundary axis of the second zone; and determining a third angle diverging from the radar sensor of the monitoring device in the second position, wherein the third angle is formed by the first boundary axis of the second zone and a second boundary axis of the second zone, wherein the second zone comprises a region between the first boundary axis and the second boundary axis.

10. The method of claim 8, further comprising:

identifying a location within the first zone, wherein the location corresponds to a subset of radar signals having a highest relative signal strength of a historical radar signal set associated with the first zone;

determining a first angle diverging from the radar sensor of the monitoring device, wherein the first angle having a first angle value determined by adding a first offset angle value to a value of an axis of the monitoring device aligned with the location within the first zone; and determining a second angle diverging from the radar sensor of the monitoring device, wherein the second angle is formed by a first boundary axis and a second boundary axis located at a second offset angle value relative to the first boundary axis, wherein the second angle corresponds to the second zone.

11. A non-transitory computer-readable storage device storing computer-executable instructions that, if executed by a processing device of a monitoring device, cause the processing device to:

detect, by a radar sensor of the monitoring device, a first set of radar signals associated with respiratory movements of at least one of a first user and a second user within a first zone comprising at least a portion of a bed;

detect, by the radar sensor at a first time, a second set of radar signals associated with first motion of the first user in a second zone located adjacent to a first side of the bed;

detect, by the radar sensor at a second time, a third set of radar signals associated with second motion of the first user in the second zone located adjacent to the first side of the bed;

identify a portion of the first set of radar signals corresponding to a time period between the first time and the second time;

generate a modified first set of radar signals by removing the portion of the first set of radar signals from the first set of radar signals; and generate a sleep-related analytic associated with the first user using the modified first set of radar signals.

12. The non-transitory computer-readable storage device of claim 11, the processing device further to:

determine a first value of a bore axis of the monitoring device in a first position;

determine a second value of the bore axis of the monitoring device in a second position;

determine a first angle value of the monitoring device in the second position using the first value and the second value;

determine a second angle value based on the first angle value, wherein the second angle value is a difference between a right angle value and the first angle value; and determine a third angle value based on the second value of the bore axis of the monitoring device, the second angle value and an offset angle value, wherein the third angle value corresponds to the second zone.

13. The non-transitory computer-readable storage device of claim 11, the processing device further to:

determine a first value of a bore axis of the monitoring device in a first position wherein the bore axis of the monitoring device is in a substantially perpendicular alignment with the first side of the bed;

determine a second value of the bore axis of the monitoring device in a second position wherein the bore axis of the monitoring device is substantially aligned with a respiratory zone within the first zone;

determine a first angle diverging from the radar sensor of the monitoring device in the second position, wherein the first angle is formed by the first value of the bore axis of the monitoring device in the first position and the second value of the bore axis of the monitoring device in the second position;

determine a second angle diverging from the radar sensor of the monitoring device in the second position, wherein the second angle is formed by the second value of the bore axis of the monitoring device in the second position and a first boundary axis of the second zone; and determine a third angle diverging from the radar sensor of the monitoring device in the second position, wherein the third angle is formed by the first boundary axis of the second zone and a second boundary axis of the second zone, wherein the second zone comprises a region between the first boundary axis and the second boundary axis.

14. The non-transitory computer-readable storage device of claim 11, the processing device further to:

identify a location within the first zone associated with a respiratory zone of the first user;

determine a first angle diverging from the radar sensor of the monitoring device, wherein the first angle having a first angle value determined by adding a first offset angle value to a value of an axis of the monitoring device aligned with the location within the first zone associated with the respiratory zone; and determine a second angle diverging from the radar sensor of the monitoring device based on the first angle and a second offset angle value, wherein the second angle corresponds to the second zone.

15. The non-transitory computer-readable storage device of claim 11, the processing device further to:

identify a location within the first zone associated with a respiratory zone of the first user, wherein the location corresponds to a subset of radar signals having a highest relative signal strength of a historical radar signal set associated with the first zone;

determine a first angle diverging from the radar sensor of the monitoring device, wherein the first angle having a first angle value determined by adding a first offset angle value to a value of an axis of the monitoring device aligned with the location within the first zone associated with the respiratory zone; and determine a second angle diverging from the radar sensor of the monitoring device, wherein the second angle is formed by a first boundary axis and a second boundary axis located at a second offset angle value relative to the first boundary axis, wherein the second angle corresponds to the second zone.

16. The non-transitory computer-readable storage device of claim 11, the processing device further to:

determine a first value of a bore axis of the monitoring device in a first position, wherein a front of the monitoring device is substantially parallel with an edge of the first side of the bed;

determine that the monitoring device is in a second position;

measure, by a sensor of the monitoring device in the second position, an angular rotation value between the first position and the second position;

determine a first angle value based on the angular rotation value;

determine a second angle value based on the first angle value, wherein the second angle value is a difference between a right angle value and the first angle value; and generate the second zone by adding an offset angle value to the second angle value.

* * * * *